US00PP26375P2

(12) United States Plant Patent
Verlinden

(10) Patent No.: US PP26,375 P2
(45) Date of Patent: Feb. 2, 2016

(54) ***VERBENA* PLANT NAMED 'VEAZ0018'**

(50) Latin Name: *Verbena hybrida*
Varietal Denomination: VEAZ0018

(71) Applicant: SYNGENTA PARTICIPATIONS AG, Basel (CH)

(72) Inventor: Kathryn Verlinden, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 136 days.

(21) Appl. No.: 14/120,138

(22) Filed: Apr. 30, 2014

(51) Int. Cl.
*A01H 5/02* (2006.01)

(52) U.S. Cl.
USPC ..... Plt./308

(58) Field of Classification Search
USPC ..... Plt./308
See application file for complete search history.

(56) References Cited

PUBLICATIONS

UPOV hit on a verben named 'VEAZ0018', QZ PBR 39723, published Aug. 16, 2013.*

* cited by examiner

*Primary Examiner* — Anne Grunberg
(74) *Attorney, Agent, or Firm* — Joshua L. Price

(57) ABSTRACT

A new *Verbena* plant named 'VEAZ0018' particularly distinguished by the large, light purple and white, bi-colored inflorescences, dark green foliage, only moderately incised leaves, and an outwardly spreading and trailing plant habit.

1 Drawing Sheet

Latin name of the genus and species of the plant claimed: *Verbena hybrida.*

Varietal denomination: 'VEAZ0018'.

BACKGROUND OF THE NEW PLANT

The present invention comprises a new *Verbena*, botanically known as *Verbena hybrida*, and hereinafter referred to by the variety name 'VEAZ0018'.

'VEAZ0018' is a product of a planned breeding program. The new cultivar has large, light purple and white, bi-colored inflorescences, dark green foliage, only moderately incised leaves, and an outwardly spreading and trailing plant habit.

'VEAZ0018' originated from a hybridization made in July 2010 in a greenhouse in Enkhuizen, The Netherlands. The female parent was an unpatented proprietary plant designated 'M0128-1', having purple-violet and white flower color and a compact trailing plant habit.

The male parent of 'VEAZ0018' was an unpatented proprietary plant designated '2153-2', having purple-violet flower color and an upright, freely branching plant habit The resulting seed was sown in February 2011 in a greenhouse in Enkhuizen, The Netherlands. 'VEAZ0018' was selected as one flowering plant within the progeny of the stated cross in May 2011.

The first act of asexual reproduction of 'VEAZ0018' was accomplished when vegetative cuttings were propagated from the initial selection in June 2011 in a greenhouse in Enkhuizen, The Netherlands.

BRIEF SUMMARY OF INVENTION

Horticultural examination of plants grown from cuttings of the plant initiated in the autumn of 2011, and continuing thereafter, has demonstrated that the combination of characteristics as herein disclosed for 'VEAZ0018' are firmly fixed and are retained through successive generations of asexual reproduction.

'VEAZ0018' has not been observed under all possible environmental conditions. The phenotype may vary significantly with variations in environment such as temperature, light intensity, and day length.

A Plant Breeder's Right for this cultivar was applied for in the Community Plant Variety Office on May 3, 2013, No. 2013/1231. 'VEAZ0018' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0018' with colors being as true as possible with an illustration of this type.

Figure 1:
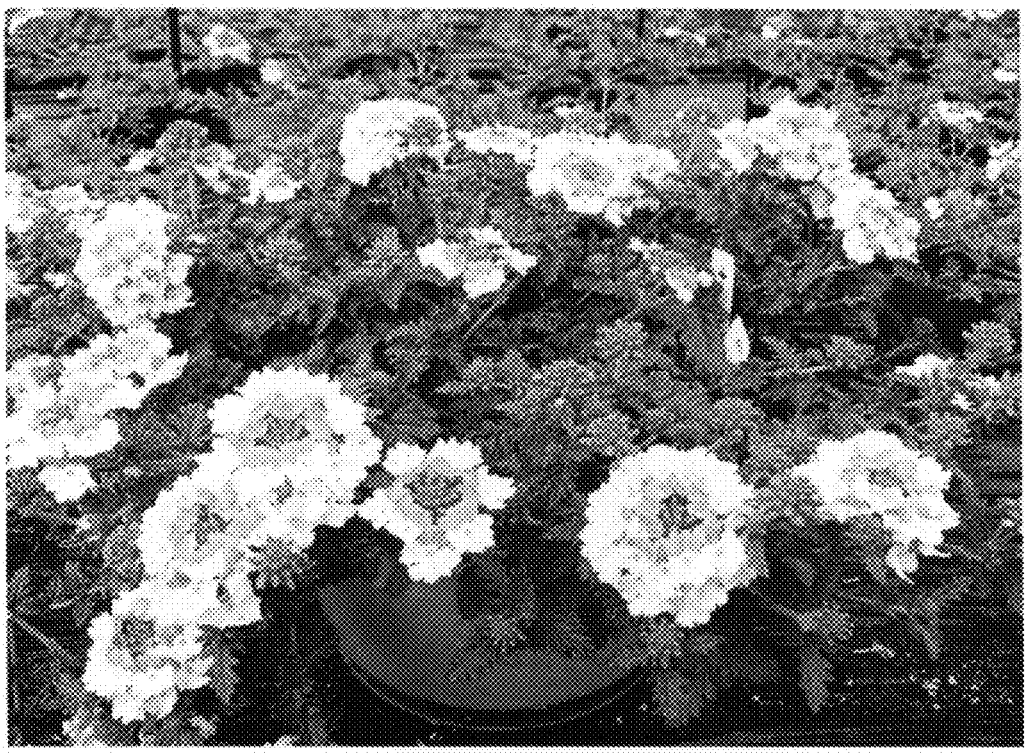
Figure 2:
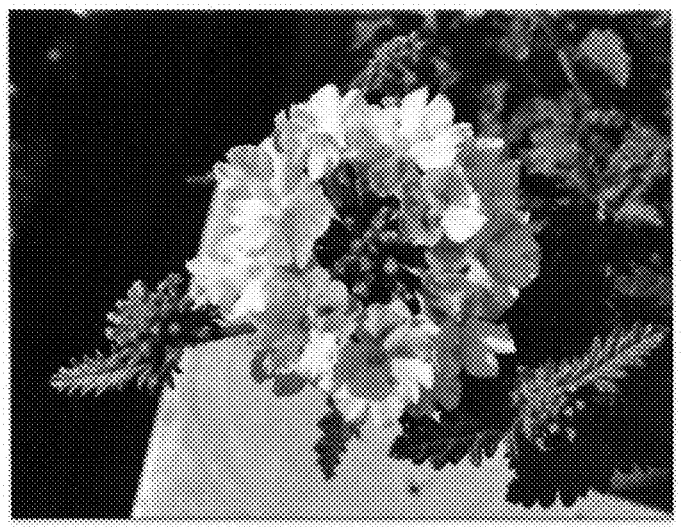

The photographic drawing in FIG. 1 shows flowering plants of the new variety in baskets, holding 3 plants each; and in FIG. 2 a close-up of the inflorescence.

DETAILED BOTANICAL DESCRIPTION

The plant descriptions and measurements were taken in Enkhuizen, The Netherlands on Apr. 8, 2014 in a greenhouse in Andijk, The Netherlands. The plants used were about 10 weeks of age and growing in 35 cm diameter hanging baskets placed on benches.

The aforementioned photographs were taken in April 2014 in Andijk, The Netherlands. The same greenhouse plants were used, as described above.

Color references are made to The Royal Horticultural Society Colour Chart (R.H.S.) 2001.

TABLE 1

DIFFERENCES BETWEEN THE NEW VARIETY 'VEAZ0018' AND A MOST SIMILAR VARIETY

| | 'VEAZ0018' | 'VEAZ0012' (U.S. Plant Pat. No. 23,659) |
|---|---|---|
| Inflorescence, shape: | Larger, and almost flat | Smaller, more mounded |
| Flower color: | Light purple and white | Purple-violet, pale purple and white |
| Leaf, size: | Larger | Smaller |

Plant:

*Form, growth and habit.*—Herbaceous, initially semi-upright, then outwardly spreading and trailing, vigorous and free-branching.

*Plant height.*—11.0 cm.

*Plant height (inflorescence included).*—15.0 cm.

*Plant width.*—49.0 cm.

Roots:

*Number of days to initiate and produce roots.*—11-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 139A.

*Immature, leaf color, lower surface.*—RHS 137D.

*Mature, leaf color, upper surface.*—RHS 137A.

*Mature, leaf color, lower surface.*—RHS 137D.

*Length.*—Approximately 5.0 cm.

*Width.*—3.6-4.0 cm.

*Shape.*—Hastate.

*Base shape.*—Rounded or obtuse.

*Apex shape.*—Obtuse.

*Margin.*—Dentate, with moderately deep incisions.

*Texture, upper surface.*—Pubescent.

*Lower surface.*—Pubescent.

*Color of veins, upper surface.*—RHS 145A.

*Color of veins, lower surface.*—RHS 145A.

*Pattern of veining.*—Pinnate.

*Petiole color.*—RHS 145A.

*Petiole length.*—0.5 cm.

*Petiole width.*—0.3 cm.

*Texture.*—Hirsute.

Stem:

*Branching characteristics.*—Side branches develop potentially at each node.

*Quantity of main branches per plant.*—4-6.

*Color of stem.*—RHS 143A.

*Stem length.*—About 17.0-21.0 cm.

*Stem width.*—About 0.25 cm.

*Length of internodes.*—About 2-3 cm.

*Texture.*—Hirsute.

*Color of peduncle.*—RHS 138A.

*Length of peduncle.*—From 2.0-5.0 cm.

*Peduncle diameter.*—0.2 cm.

*Texture.*—Canescent, also short, transparent glandular hairs.

Inflorescence:

*Type.*—Umbel-like, but actually a spike, umbrella-shaped.

*Blooming habit.*—Flowers continuously during the summer months.

*Lastingness of individual blooms on the plant.*—About 4-5 days in the greenhouse.

*Fragrance.*—None.

*Number of inflorescences per plant.*—46 at various stages at development.

*Horizontal diameter of inflorescence.*—5.8-6.2 cm.

*Depth of inflorescence.*—3.5 cm.

*Number of florets and buds per inflorescence.*—Approximately 39-42.

Bud (just when opening/showing color):

*Color.*—RHS N155A with blushes of RHS 75D.

*Length.*—0.4 cm (future corolla only).

*Width.*—0.4 cm.

*Shape.*—Tubular with bulbous apex.

Floret:

*Form.*—Sessile; salver-shaped, composed of 5 partly fused petals with a base of a narrow tube.

*Immature color, 2 top petals, upper surface.*—RHS N74C with shades of N74A.

*Immature color, 2 top petals, lower surface.*—RHS 73C.

*Immature color, 3 lower petals, upper surface.*—RHS150C mainly, and possibly RHS 73B near the edges.

*Immature color, 3 lower petals, lower surface.*—RHS N155A.

*Mature color, 2 top petals, upper surface.*—RHS N74C with shades of N74B.

*Mature color, 2 top petals, lower surface.*—RHS 73C.

*Mature color, 3 lower petals, upper surface.*—RHS 155A mainly, and possibly RHS 73B near the edges.

*Mature color, 3 lower petals, lower surface.*—RHS N155A.

*Floret diameter.*—2.2 cm.

*Floret length (depth).*—2.4 cm.

*Petal length.*—1.0 cm.

*Petal width.*—1.1 cm.

*Shape.*—Ob-cordate.

*Apex shape.*—Emarginate.

*Margin.*—Entire.

*Petal texture, upper surface.*—Papillose; a little glandular hair.

*Petal texture, lower surface.*—Papillose, pubescent.

*Corolla tube length.*—2.1 cm.

*Corolla tube width.*—0.2 cm.

*Corolla tube color inside.*—RHS 150D.

*Tube color outside.*—RHS 150C to RHS 145D at upper end.

*Corolla texture, inside.*—Pubescent, longer and shorter hairs.

*Corolla texture, outside.*—Canescent, lower part glabrous.

*Throat hair color.*—RHS 155D but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 143A.

*Length of sepals.*—1.2 cm.

*Width of sepals.*—0.2 cm.

*Sepal shape.*—Fused, linear.

*Apex shape.*—Acute.

*Margins.*—Entire.

*Texture*.—Densely covered with short hair, and with very short glandular hair.

Reproductive organs:

*Gynoecium*.—Pistil: 1. Pistil length: 1.8 cm. Style color: RHS-N144D. Style length: 1.6 cm. Stigma color:. RHS 144A. Ovary color:. RHS 144B. Ovary length: 0.2 cm. Ovary width: 0.1. cm.

*Androecium*.—Stamens: Anthers and filaments fused to upper half of corolla tube; four anthers with two pollen sacs per anther. Color of filaments: RHS 151D. Filament length: 0.2 cm. Anther color: RHS 151C. Anther length: 0.15 cm. Pollen amount: None observed.

Fertility/seed set: Has not been determined to date.

Disease/pest resistance: Has not been determined to date.

What is claimed is:

1. A new and distinct variety of *Verbena* plant named 'VEAZ0018' substantially as illustrated and described herein.

* * * * *